US010086051B2

(12) United States Patent
Cullmann et al.

(10) Patent No.: US 10,086,051 B2
(45) Date of Patent: Oct. 2, 2018

(54) USE OF HYALURONIDASE FOR THE PREVENTION OR TREATMENT OF ARTERIAL HYPERTENSION OR CARDIAC INSUFFICIENCY

(75) Inventors: Dieter Cullmann, Zweibrücken (DE); Gunther Burgard, Homburg (DE)

(73) Assignee: PANTARHIN PHARMA LLC, Naples, FL (US)

( * ) Notice: Subject to any disclaimer, the term of this patent is extended or adjusted under 35 U.S.C. 154(b) by 1376 days.

(21) Appl. No.: 12/578,354

(22) Filed: Oct. 13, 2009

(65) Prior Publication Data
US 2010/0092450 A1 Apr. 15, 2010

(30) Foreign Application Priority Data

Oct. 14, 2008 (EP) .................................... 08017979

(51) Int. Cl.
*A61K 38/47* (2006.01)
*A61K 38/55* (2006.01)
*A61K 45/06* (2006.01)
(52) U.S. Cl.
CPC ............ *A61K 38/47* (2013.01); *A61K 38/556* (2013.01); *A61K 45/06* (2013.01)
(58) Field of Classification Search
None
See application file for complete search history.

(56) References Cited

U.S. PATENT DOCUMENTS

2005/0249717 A1    11/2005  Burgard et al.

FOREIGN PATENT DOCUMENTS

| NL | 8102880 | * | 1/1983 |
|----|---------|---|--------|
| WO | 98/08538 | | 3/1998 |
| WO | 99/29841 | | 6/1999 |
| WO | WO 0191785 A2 | | 12/2001 |
| WO | 05/078140 | | 8/2005 |

OTHER PUBLICATIONS

Rauchova et al., European Journal of Pharmacology 342 (1998). 235-239.*
Abstract of NL 8102880 (Jan. 17, 1983).*
De Oliveira et al., Am. Heart Journal, 1959, vol. 57, pp. 712-722.*
Gilyova et al., Russian Journal of Biomechanics, vol. 3, No. 4: pp. 1-10, 1999.*
Ryan, J.J., "The Treatment of Hypertension by Hyaluronidase", published by Milne Publishers, Brisbaine, 1954, pp. 132-142.*
Hansen. Die beinflussing der resorption von subcutan injizierte 14C-lidocain durch hyaluronidase and adrenalin beim merrschweinchen. Archiv Fur Klinische Und Experimentelly Ohren- Nasen- Und Kehkopfheilkunde, 1967, vol. 188, No. 2, pp. 552-555.
Nara et al. Contribution of interstitial diffusion in drug absorption from perfused rabbit muscle: effect of hyluronidase on absorption. Chemical and Pharmaceutical Bulletin. 1992, vol. 40, No. 3, pp. 737-740.
Srivastava et al. Biochemical basis to block ischaemia developing into myocardial infarction: a short review. Journal of the Indian Institute of Science. Section C., 1981, vol. 63, No. 4, pp. 53-69.
Hansen. Die beinflussing der resorption von subcutan injizierte 14C-lidocain durch hyaluronidase and adrenalin beim merrschweinchen. Archiv Fur Klinische Und Experimentelly Ohren- Nasen- Und Kehkopfheilkunde, 1967, vol. 188, No. 2, pp. 552-555. (Translation included).
Johnsson et al., "Edema Treatment During Cardiac Allograft Rejection", Journal of Heart and Lung Transplantation 18 (1999), p. 1238-1242.
Madan et al., "A Dose Response Study of Clonidine with Local Anesthetic Mixture for Peribulbar Block: A Comparison of Three Doses", Anesth. Analg. 93 (2001), p. 1593-1597.
Mashkovsky, "Lekarstvennye sredstva", Novaya Volna (2005), 444-445.
Vertkin, et al., "Acute Cardiac Insufficiency. Diagnosing and Pre-Clinical Treatment.", Lechashchii vrach (2002), 9:71-76.
Alexander; "Theodore Cooper Memorial Lecture. Hypertension and the pathogenesis of atherosclerosis. Oxidative stress and the mediation of arterial inflammatory response: a new perspective"; Hypertension; vol. 25, No. 2, pp. 155-161 (Feb. 1995).
Ehret, et al.; "Genetic variants in novel pathways influence blood pressure and cardiovascular disease risk"; Nature; vol. 478, No. 7367, pp. 103-109 (Sep. 11, 2011).
Fruchart, et al.; "New Risk Factors for Atherosclerosis and Patient Risk Assessment"; Circulation; vol. 109, Suppl. III, III-15-III-19 (2004).
Jackson; "Which elderly patients should be considered for antihypertensive treatment? An evidence-based approach"; Journal of Human Hypertension; vol. 12, pp. 607-613 (1998).
Lifton, et al.; "Molecular Mechanisms of Human Hypertension"; Cell; vol. 104, pp. 545-556 (Feb. 23, 2001).
Rimoldi, et al.; "Secondary arterial hypertension: when, who, and how to screen?" European Heart Journal; DOI:10.1093/eurheartj/eht534; pp. 1-12 (Dec. 23, 2013).
Sorof, et al.; "Obesity Hypertension in Children, A Problem of Epidemic Proportions"; Hypertension; vol. 40, No. 4, pp. 441-447 (Oct. 2002).
Vasan, et al.; "Residual Lifetime Risk for Developing Hypertension in Middle-Aged Women and Men"; JAMA; vol. 287, No. 8, pp. 1003-1010 (Feb. 27, 2002).
Whitworth; "Blood pressure and control of cardiovascular risk"; Vasc. Health Risk Manag.; vol. 1, No. 3, pp. 257-260 (Sep. 2005).

(Continued)

*Primary Examiner* — Irene Marx
(74) *Attorney, Agent, or Firm* — Bozicevic, Field & Francis LLP; Paula A. Borden

(57) ABSTRACT

The present invention relates to the use of hyaluronidase for the prevention and/or treatment of arterial hypertension or cardiac insufficiency. In addition, the present invention provides a composition and a combined preparation each comprising hyaluronidase and at least one further antihypertensive, and a method of prevention and/or treating arterial hypertension or cardiac insufficiency in a patient in need thereof, wherein the patient is administered a therapeutically effective amount of hyaluronidase.

20 Claims, No Drawings

(56) References Cited

OTHER PUBLICATIONS

Williams, et al.; "The Response-to-Retention Hypothesis of Early Atherogenesis"; Arterioscler Thromb Vasc Biol.; vol. 15, No. 5, pp. 551-561 (May 1995).

* cited by examiner

USE OF HYALURONIDASE FOR THE PREVENTION OR TREATMENT OF ARTERIAL HYPERTENSION OR CARDIAC INSUFFICIENCY

CROSS-REFERENCE

This application claims the benefit of European Patent Application No. 08017979.9, filed Oct. 14, 2008, which application is incorporated herein by reference in its entirety.

FIELD OF THE INVENTION

The present invention relates to the use of hyaluronidase for the prevention and/or treatment of arterial hypertension or cardiac insufficiency. In addition, the present invention provides a composition and a combined preparation each comprising hyaluronidase and at least one further antihypertensive, and a method of prevention and/or treating arterial hypertension in a patient in need thereof, wherein the patient is to be administered a therapeutically effective amount of hyaluronidase.

Arterial hypertension being associated with elevated arterial pressure is one of the most important public health problems in developed countries. Approximately one in four adults in the western world suffers from hypertension. It is common, readily detectable, and often leads to serious consequences, including renal disease, myocardial infarction (MI), and cerebrovascular accident or even lethal complications if left unattended. The understanding of the pathophysiology of hypertension has increased over the last decade but in many cases the etiology is still largely unknown. Thus, hypertension is often treated non-specifically, resulting in a large number of side effects and a relatively high non-compliance rate.

A number of antihypertensives are known in the art that are used to treat arterial hypertension such as diuretics, alpha-adrenergic receptor inhibitors, beta adrenergic receptor inhibitors, angiotensin converting enzyme (ACE) inhibitors, angiotensin receptor inhibitors, calcium-channel inhibitors, vasodilatating agents, and antisympathotonics. However, most of these medicaments are associated with side effects or are not applicable to all kinds of arterial hypertensions. For example, for beta adrenergic receptor inhibitors asthma is generally considered to be a contraindication. Furthermore, peripheral vascular disease and bradycardia are relative contraindications for beta adrenergic receptor inhibitors and in susceptible patients, heart block and heart failure may be initiated. Thiazide diuretics show side-effects such as hypokalemia, dyslipidemia, and gout. Calcium-channel antagonists such as short-acting dihydropyridines are associated with an increased risk of myocardial infarct at high doses and longer-acting calcium-channel antagonists show side effects including ankle edema, headache, and flushing. Renin/angiotensin system antagonists such as ACEs and angiotensin type 1 receptor antagonists may lead to renal artery stenosis. Alpha-adrenergic receptor antagonists may be associated with palpitations and occasional postural hypotension as side effects. As a consequence, there is a need for an effective anti-hypertensive that is well tolerated by patients as it shows little or no side-effects. Moreover, it is of advantage if life-long administration of antihypertensives can be avoided.

Moreover, an effective treatment regimen has to be adapted to the type of arterial hypertension which a particular patient suffers from, often requiring the administration of more than one antihypertensive. In addition, the effective medication of hypertension for patients suffering from the same kind of hypertension may have to be adapted to the individual patient. As a result, there is a need for a further antihypertensive to broaden the spectrum of antihypertensives to choose from.

Hyaluronidase belongs to the so-called beta (1-4)-glycosidases. These enzymes are also designated as hyaluronate glycan hydrolases, EC 3.2.1.35 through 3.2.1.36. Hyaluronidase hydrolyses hyaluronic acid, a linear heteroglycan with alternating glucuronic acid and N-acetyl-glucosamine residues (acidic glycosaminoglycan (mucopolysaccharide)) and hyaluronate (the ionic form of hyaluronic acid) but also does the same to chondroitin sulphate. Hyaluronidase has been implicated in the treatment of cardiovascular diseases such as arteriosclerosis but it was hitherto unknown that hyaluronidase may have an impact on the blood pressure.

One of the objects of the present invention is to provide a means for the prevention and/or treatment of arterial hypertension or cardiac insufficiency that avoids at least one of the disadvantages associated with the antihypertensives known in the art and/or that improves the therapy of arterial hypertension or cardiac insufficiency. It is another object to provide a means for the prevention and/or treatment of arterial hypertension or cardiac insufficiency that can be combined with at least one of the known antihypertensives to improve the prevention and/or treatment of arterial hypertension or cardiac insufficiency.

SUMMARY OF THE INVENTION

At least one of the aforementioned objects is solved by using hyaluronidase for the prevention and/or treatment of arterial hypertension or cardiac insufficiency. Preferably hyaluronidase is used for the prevention in a risk patient selected from a patient suffering from obesity, a patient with a positive infarct anamnesis, a patient with a positive stroke anamnesis and a patient with a family history of arterial hypertension. Additional advantageous and preferred embodiments of the invention will be described in the following.

Herein below the invention is described in more detail without limitation.

The present invention is based on the surprising result that administration of hyaluronidase effectively reduces the elevated blood pressure in patients suffering from arterial hypertension. While it was known in the field that hyaluronidase removes arteriosclerotic plaques, this phenomenon cannot explain the surprising blood pressure-lowering effect of hyaluronidase. This is consistent with the fact that presence of plaques and sclerotic vasculature on one hand and hypertension on the other hand are dissociated events as it can, for example, be concluded from the observation that even though all humans can develop plaques and sclerotic vasculature with increasing age, there is no correlation between the amount of plaques or sclerotified vessels and the occurrence of hypertension. This is also consistent with the finding that as a result of the Hyaluronidase treatment the present inventors observed a sustained and significant reduction in arterial hypertension in hypertensive patients who displayed no significant arteriosclerotic plaques before and after commencement of the Hyaluronidase treatment.

Without wishing to be bound to any theory, it appears that in response to an increased blood pressure, the extracellular matrix of the blood vessels is enforced. This pressure-induced enforcement of the vascular extracellular matrix is inter alia effected by the increased presence of chondroitin-4-sulfate and/or chondroitin-6-sulfate chains. In the long run the enforcement of the vasculature's extracellular matrix results in a hardening of the vessels which in turn leads to an increase in blood pressure. Hyaluronidase exerts its blood pressure-reducing effect by contributing to the breaking down of the excessively enforced vascular extracellular matrix and preferably, of the chondroitin-4-sulfate and/or chondroitin-6-sulfate chains which ultimately results in a more flexible vasculature and a decrease in blood pressure. In addition, Hyaluronidase preferably exerts its effect by hydrolyzing hyaluronic acid which is part of the backbone of the proteoglycans.

Apart from rare allergic reactions against Hyaluronidase, only bacterial infection are known as a contraindication for a hyaluronidase-based treatment. Thus, hyaluronidase-based treatment avoid a large number of side effects and limitation associated with the antihypertensives known in the art.

Cardiac insufficiency may result from an ongoing or chronic arterial hypertension due to consecutive pressure load on the heart muscle. By lowering the blood pressure hyaluronidase surprisingly allows for an effective treatment of cardiac insufficiency.

As it is used herein "arterial hypertension" preferably means a medical condition where the blood pressure is elevated, preferably the blood pressure is elevated chronically. An "elevated blood pressure" as used herein refers to a blood pressure that in a human resting adult patient is about 140-150/about 90-100 mmHg [systolic pressure/diastolic pressure mmHg] or more, preferably about 150-170/about 100-110 mmHg or more, most preferably about 170/about 110 mmHg or more. Preferably, an "elevated blood pressure" is a systolic blood pressure of at least about 140 mmHg and/or a diastolic blood pressure of at least about 90 mmHg. The blood pressure is preferably elevated chronically, i.e. preferably this condition lasts for more than about 1, about 2, about 3 or about 4 weeks, more preferably for more than about 1, about 2, about 3, about 4, about 5 or about 6 months, most preferably more than about half a year, about 1, about 2, about 3, about 4, about 5, about 6, about 7, about 8, about 9 or about 10 years, preferably the condition lasts continuously throughout the indicated period of time. It is generally known how to determine whether the blood pressure is chronically elevated. For example, the blood pressure may be measured at regular intervals such as one or more times every day, every other day, etc. under comparable conditions such as at the same time of the day.

The blood pressure can be determined by methods generally known such as by direct (invasive) measurement, such as through an arterial line, or by indirect measurement, such as by Doppler-sonographic methods, oscillometric methods or by an auscultatory method, especially by using a sphygmomanometer. It is preferred that the blood pressure is measured by the Riva-Rocci method.

These methods can also be used to determine the success of the therapy of the present invention. Preferably, the treatment according to the present invention is considered to be effective if in response to the Hyaluronidase treatment the diastolic blood pressure is reduced by at least about 5 mmHg, preferably at least about 10 mmHg, preferably at least about 15 mmHg, preferably at least about 20 mmHg, preferably at least about 30 mmHg, more preferably at least about 40 mmHg, most preferably at least about 50 mmHg. Moreover, the treatment according to the present invention is considered to be effective if in response to the Hyaluronidase treatment the systolic blood pressure is reduced by at least about 5 mmHg, preferably at least about 10 mmHg, preferably at least about 15 mmHg, preferably at least about 20 mmHg, preferably at least about 30 mmHg, more preferably at least about 40 mmHg, most preferably at least about 50 mmHg. Most preferably, in response to the Hyaluronidase treatment the diastolic blood pressure falls to a value of about 80 to about 70 mmHg or less and/or the systolic blood pressure falls to a value of less than about 130 mmHg.

According to a preferred embodiment, hyaluronidase is used for the treatment of an arterial hypertension selected from the group consisting of endocrine hypertension, essential hypertension, arteriosclerotic hypertension, cardiovascular hypertension, renal hypertension, labile hypertension, neurogenic hypertension, paroxysmal hypertension, portal hypertension, pulmonary hypertension, and secondary hypertension. Also encompassed by "arterial hypertension" as used herein is a hypertension caused by monogenic defects such as glucocorticoid-remediable aldosteronism and Liddle's syndrome, hypertension caused by hypertension-susceptilibity genes such as angiotensinogen and alpha-adducin genes. "Arterial hypertension" according to the invention may as well be caused by environmental factors such as salt intake, preferably sodium intake, obesity, occupation, and alcohol intake, all of which forms of hypertension are also contemplated as being encompassed by the present invention. Moreover, hypertension in the sense of the present application also includes hypertension caused by obstructive sleep apnea, by aortic coarctation, by pre-eclampsia, by drugs such as combined oral contraceptive pill, cyclosporin, steroids, and by CNS disturbances.

"Arteriosclerotic hypertension" is a form of arterial hypertension which is preferably associated with a progressive increase in muscle and elastic tissue of arterial walls, resulting from hypertension; in longstanding arteriosclerotic hypertension, elastic tissue forms numerous concentric layers in the intima and there is replacement of muscle by collagen fibers and hyaline thickening of the intima of arterioles; such changes can develop with increasing age in the absence of hypertension and may then be referred to as senile arteriosclerosis. In arteriosclerotic hypertension, hypertension generally results from reduced Windkessel function and an increase in the elastic vascular resistance.

"Cardiovascular hypertension" preferably results from an illness of the heart or of vessels close to the heart, in particular of the aorta, usually from an increased stroke volume and minute volume and reduced expansibility of the vessel, in particular the Windkessel function. Typical illnesses are aortic valve insufficiency, aortic isthmus stenosis and aortic atheromatosis.

"Renal hypertension" preferably includes renal artery stenosis, polycystic kidney disease, chronic reflux nephropathy, chronic glomerulonephritis, polyarteritis nodosa and systemic sclerosis.

"Endocrine hypertension" as used herein preferably refers to an arterial hypertension caused by an excess of hormone-production such as in the case of primary hyperaldosteronism, congenital or hereditary adrenogenital syndromes, pheochromocytoma, myxedema, acromegaly, Conn-syndrom, Cushing-syndrom, toxemia of pregnancy, hyperparathyroidism, polycystic ovarian syndrome, metabolic syndrome such as diabetes mellitus, dyslipidemia and obesity.

"Essential hypertension" as used herein preferably refers to arterial hypertension in patients without a medical cause that can be attributed to the hypertension. It is generally associated with an increased flow resistance due to functional and/or organic constriction of the arterial vessels and arterioles. Essential hypertension is promoted by a hereditary disposition, constitution (e.g. obesity), akinesia, and psychological strains. As used herein, in case there is a known cause for the arterial hypertension such as an illness, damage or impairment of an organ, the hypertension is preferably referred to as "secondary hypertension".

"Labile hypertension" as used herein preferably refers to arterial hypertension with transient periods of normal blood pressure.

"Neurogenic hypertension" as used herein preferably relates to an arterial hypertension resulting from an impairment or damage to the peripheral and/or central neural structures involved in the regulation of the circulatory regulation. Neurogenic hypertension includes aortic arch syndrome, hypertension following or associated with (i) an injury of the cranium, preferably an injury of the cranium and of the cranial nerves IX or X, (ii) brain tumor, (iii) polyneuropathy, (iv) meningitis, (v) poliomyelitis, (vi) intoxications, (vii) injury or damaging of the medulla oblongata, (viii) diencephalic syndrome, (ix) spinal chord section, and (x) increased intracranial pressure.

"Portal hypertension" as used herein preferably is an arterial hypertension in the portal vein and its branches. It is generally defined as a portal pressure gradient (the difference in pressure between the portal vein and the hepatic veins) of 5 mm Hg or greater. Many conditions can result in portal hypertension. In North America and Europe, it is usually the result of cirrhosis of the liver. However, in less industrialized parts of the world, schistosomiasis is a major cause of portal hypertension.

"Pulmonary hypertension" as used herein preferably is an increase in blood pressure in the pulmonary artery, pulmonary vein, or pulmonary capillaries, together known as the lung vasculature, leading to shortness of breath, dizziness, fainting, and other symptoms, all of which are exacerbated by exertion. The most common cause of pulmonary hypertension is left heart failure leading to pulmonary venous hypertension. Other common causes of pulmonary arterial hypertension include HIV, scleroderma, autoimmune disorders, cirrhosis and portal hypertension, sickle cell disease and congenital heart disease.

"A patient with a family history of arterial hypertension" as used herein preferably relates to a patient where at least one, preferably at least 2, preferably at least 3, preferably at least 4, more preferably at least 5, most preferably at least 6 members of the patient's family of the same generation and/or of a previous generation suffered from arterial hypertension.

"A patient with a positive infarct anamnesis" as used herein preferably is a patient who has been diagnosed as suffering from an infarct, preferably from a myocardial infarct.

"A patient with a positive stroke anamnesis" as used herein preferably is a patient who has been diagnosed as suffering from a stroke and/or from ischemia.

The hyaluronidase can of course not only be used to therapy an already existing arterial hypertension but also for preventive treatment, that is prophylactically, for the indications cited above in order to avoid or delay the occurrence of such disorders.

The "hyaluronidase" of the present invention can be derived from any source whatsoever. For example, the hyaluronidase may be derived from a mammal such as from human, mouse, rat, pig, sheep or cow. For instance, the hyaluronidase may be recovered from bovine protein (bovine type), alternatively from leeches or bacteria (e.g. in the form of hyaluronate lyase). The hyaluronidase can also be of vegetable origin. The hyaluronidase can be isolated, for instance, from potatoes, tobaccos and peas. Purification, chemical synthesis and genetic engineering techniques including production in a transgenic host generally known in the art can likewise be used to produce hyaluronidase. Particularly preferred is any hyaluronidase which splits and thus depolymerises hyaluronic acid, chondroitin-4-sulphate, chondroitin-6-sulphate and mucotin sulphate where the most preferred hyaluronidase is an enzyme available commercially such as, by way of example, the hyaluronidase marketed under the trade name of "Hylase Dessau" by RIEMSER Arzneimittel A G, preferably Hylase Dessau 1500 IU by RIEMSER Arzneimittel AG, containing 1500 IU of bovine hyaluronidase. For prevention and/or treatment of the disorders of the present invention, a mixture of hyaluronidases of different origins can also be used. When using other hyaluronidases than Hylase Dessau other dosages may be required which the person skilled in the art can easily determine according to the practical circumstances of the case.

According to a preferred embodiment, the hyaluronidase is used as a prevention or treatment of the above defined arterial hypertension or cardiac insufficiency in a human or animal patient. Preferably the animal patient is a mammal, preferably a farm animal such as cattle, sheep, goat, pig, or deer, or a pet, preferably selected from cat, dog, and hamster.

According to yet another preferred embodiment, hyaluronidase is prepared for administration through the digestive tract, or parenterally. When administered through the digestive tract, hyaluronidase is preferably administered nasally, sublingually, orally, such as by way of a tablet, solution or capsule. Alternatively, hyaluronidase is to be administered parenterally, preferably through injection by intravenous, intraperitoneal, intracerebral (intraparenchymal), intracerebroventricular, intramuscular, subcutaneous, intraocular, intraarterial, intraportal, or intralesional routes; by sustained release systems or by implantation devices. Where desired, the compositions may be administered by bolus injection or continuously by infusion, or by implantation device. Preferably, hyaluronidase is to be administered intravenously.

When parenteral administration is contemplated, the therapeutic compositions for use in this invention may be in the form of a pyrogen-free, parenterally acceptable, aqueous solution comprising the desired hyaluronidase in a pharmaceutically acceptable vehicle. A particularly suitable vehicle for parenteral injection is sterile distilled water in which a hyaluronidase is formulated as a sterile, isotonic solution, properly preserved, preferably as isotonic solution (saline, 0.9% NaCl solution). Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Other suitable means for the introduction of hyaluronidase include implantable drug delivery devices.

According to another aspect of the present invention, it is provided a pharmaceutical composition which comprises hyaluronidase, a composition of the present invention comprising hyaluronidase and at least one further antihypertensive, or the combined preparation of the present invention comprising hyaluronidase and at least one further antihypertensive, as defined below. Preferably, the pharmaceutical composition comprises a therapeutically effective amount of hyaluronidase and preferably also a therapeutically effective amount of the at least one further antihypertensive, in admixture with at least one pharmaceutically and/or physiologically acceptable formulation agent, at least one vehicle and/or at least one carrier, the formulation agent, the vehicle and the carrier selected for suitability with the mode of administration. Such acceptable formulation agents are generally known in the art and inter alia comprise agents for modifying, maintaining, or preserving, for example, the pH, osmolarity, viscosity, clarity, color, isotonicity, odor, sterility, stability, rate of dissolution or release, adsorption, or penetration of the composition. Suitable formulation agents include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See Remington's Pharmaceutical Sciences (18th Ed., A. R. Gennaro, ed., Mack Publishing Company 1990).

The formulation components are present in concentrations that are acceptable to the site of administration. For example, buffers are used to maintain the composition at physiological pH or at a slightly lower pH, typically within a pH range of from about 5 to about 8. The optimal pharmaceutical composition according to the invention will be determined by a skilled artisan depending upon, for example, the intended route of administration, delivery format, and desired dosage. See, e.g., Remington's Pharmaceutical Sciences, supra. Such compositions may influence the physical state, stability, rate of in vivo release, and rate of in vivo clearance of the hyaluronidase.

The primary vehicle or carrier in a pharmaceutical composition according to the invention may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, hyaluronidase compositions may be prepared for storage by mixing the selected composition having the desired degree of purity with optional formulation agents (Remington's Pharmaceutical Sciences, supra) in the form of a lyophilized cake or an aqueous solution. Further, the pharmaceutical composition may be formulated as a lyophilizate using appropriate excipients such as sucrose.

According to a preferred embodiment, at least about 3,000 IU, about 4,500 IU, preferably at least about 6,000 IU, more preferably at least about 8,000 IU, even more preferably at least about 10,000 IU, most preferably at least about 15,000 IU, most preferably at least about 20,000 IU, most preferably at least about 25,000 IU, most preferably at least about 30,000 IU of hyaluronidase are administered per day.

Preferably, the Hyaluronidase dosage is increased over time until preferably a plateau dosage is reached, particularly in the initial period of the Hyaluronidase therapy. Preferably the Hyaluronidase dosage increases at an interval ranging from about 1 day to about 6 days, preferably from about 1 day to about 3 days; each dosage increase ranging from about 500 IU to about 2.500 IU, more preferably each dosage increase is about 1.500 IU, as exemplified in the dosage regimens of the Examples. Preferably, the Hyaluronidase dosage starts out from about 3.000 IU to about 4.500 IU, preferably from about 4.500 IU and is then increased over time to a dosage of about 10.000 IU to about 15.000 IU, preferable to a dosage of about 12.500 IU, preferably the dosage increases are carried out as described before. Of course the dosage increase may differ from day to day. According to a preferred embodiment the dosage may as well decrease over time, such as before the Hyaluronidase administration is discontinued.

Preferably the dose may be administered by a single administration or in more than one administration spread over 24 hours. Preferably, the expression "per day" is also meant to encompass the administration of the indicated dose on each and every day. More preferably, the term "per day" also encompasses the case where the indicated dose is to be administered on average per day, i.e. the dose may vary from day to day but the averaged dose is defined by the indicated dose "per day".

The expression "IU" as used herein preferably refers to the generally known term international unit (IU). According to a preferred embodiment hyaluronidase is to be administered from about 1 to about 7 days per week, preferably about 3 to about 7 days per week, more preferably about 5 to about 7 days per week, more preferably about 1 to about 5 days per week, more preferably about 3 to about 5 days per week.

According to a preferred embodiment hyaluronidase is to be administered at least about 1 week, at least about 2 weeks, at least about 3 weeks, at least about 4 weeks, at least about 5 weeks, at least about 6 weeks, at least about 7 weeks, at least about 8 weeks, preferably at least about 1 month, at least about 2 months, at least about 3 months, at least about 4 months, at least about 5 months or at least about 6 months. Preferably the administration is carried out continuously over the indicated time period.

Preferably, the at least about 3,000 IU hyaluronidase are to be administered per day for about 3 to about 7 days per week for at least about 2 weeks, preferably for at least about 4 weeks. Preferably the administration is carried out continuously over the indicated time period.

Of course, the concrete dosage duration can naturally be varied in each individual case and an effective treatment regimen has to be adapted to the type of arterial hypertension which a particular patient suffers from. In addition, the effective medication of hyaluronidase for patients suffering from the same kind of hypertension may have to be adapted to the individual patient.

According to yet another aspect of the invention it is provided a composition comprising hyaluronidase and at least one further antihypertensive as defined below. It is generally known how to formulate the hyaluronidase and at least one further antihypertensive. The dosage of the at least one further antihypertensive can be readily determined by the skilled physician.

It was surprisingly shown that the administration of hyaluronidase allows to reduce the dosage or even omit the use of some or all of the antihypertensives (in the sense of the at least one further antihypertensives defined herein) administered to a patient suffering from an arterial hypertension before the onset of the administration of hyaluronidase (see Examples). Thus, hyaluronidase not only reduces the blood pressure on its own but it preferably displays an additive or even synergistic effect on the anti-hypertensive activity displayed by the antihypertensives mentioned above.

The "at least one further antihypertensive" as used herein is meant to encompass any generally known antihypertensive agent, medicine, or active agent(s) contained in the aforementioned medicine which can be used to treat arterial hypertension. Preferably, the antihypertensive is selected from a diuretic agent, an alpha-adrenergic receptor inhibitor, a beta-adrenergic receptor inhibitor, an angiotensin converting enzyme inhibitor, an angiotensin receptor inhibitor, a renin inhibitor, a calcium-channel inhibitor, a vasodilatating agent, an antisympathotonic agent and an imidazoline type 1 receptor agonist. Preferably, the diuretics are thiazide diuretics, e.g. bendrofluazide. They work by inhibiting NaCl reabsorption in the distal tubule. This initially leads to an increase in Na+ loss and a reduction in plasma volume. Preferred diuretics include benzothiadiazine derivatives, carbonic anhydrase inhibitors, xanthine derivates. A preferred alpha-adrenergic receptor inhibitor is an alpha1-adrenergic receptor inhibitor, preferably Doxazosin or Prazosin. They work to reduce total peripheral resistance by blocking the sympathetic activation of α1-receptors on resistance vessels. A preferred beta (1)-adrenergic receptor inhibitor is Atenolol, Nebilit and Metoprolol. Preferred angiotensin converting enzyme (ACE) inhibitors are Captopril, Enalapril, Lisinopril, Ramipril and Perindopril. Preferred angiotensin receptor inhibitors are Atacand, Losartan, Valsartan, Eprosartan, Irbesartan, and Candesartan. Preferred $Ca^{++}$-channel inhibitors include Atacand, Nitrendipin, Nimodipin, Amlodipin, Felodipin, Verapamil-type, and Diltiazem-type. Preferred vasodilatating agent encompass hydralazine, Dihydralazin, Minoxidil, Nitroprussidnatrium, Diazoxid and Hydralazin. Preferred antisympathotonics include Reserpin, Guanethidin, Clonidin and Methyldopa. A preferred renin inhibitor is Rasilez (Aliskiren).

According to yet another aspect of the invention it is provided a combined preparation comprising hyaluronidase and at least one further antihypertensive. The combined preparation can be used for the prevention or treatment of arterial hypertension or cardiac insufficiency; wherein the hyaluronidase and the at least one further antihypertensive are preferably used for simultaneous or temporally separated administration. Preferably the combined preparation is used for the prevention in a risk patient selected from a patient suffering from obesity, a patient with a positive infarct anamnesis, a patient with a positive stroke anamnesis and a patient with a family history of arterial hypertension. In the combined preparation hyaluronidase and the at least one further antihypertensive are not present as a single composition but are rather kept as separate entities. In case at least two further antihypertensive are used each of the antihypertensives is preferably stored separate from the other antihypertensive(s). Preferably, the hyaluronidase and at least one further antihypertensive are stored in separate containers, or in separated spaces of a single container, preferably each of the at least one further antihypertensive is stored in a separate space of the single container. More preferably the at least two further antihypertensives are combined to a single composition. Preferably, hyaluronidase and preferably also the at least one further antihypertensive are stored in the container(s) in dosage unit form. Preferably, hyaluronidase and the at least one further antihypertensive are combined into a single composition before said composition is to be administered to the patient.

Hyaluronidase, the composition of the invention, the combined preparation of the invention and the pharmaceutical composition of the invention may be used for the treatment of arterial hypertension as defined above. According to a preferred embodiment of the invention, the composition comprising hyaluronidase and at least one further antihypertensive of the invention, the combined preparation of the invention and the pharmaceutical composition of the invention comprise a satane; a satane and a hydrochlorthiazid; or a rennin inhibitor, preferably aliskiren, and a statine such as Crestor (Rosuvastatin Calcium); as the at least one further antihypertensive for the treatment of arterial hypertension.

According to another aspect of the present invention, it is provided a method of preventing and/or treating arterial hypertension as defined above or cardiac insufficiency; which method comprises administering to a patient a therapeutically effective amount of hyaluronidase, of the pharmaceutical composition of the invention, of the composition of the invention or of the combined preparation of the invention, whereupon arterial hypertension in the patient is treated and/or prevented. Preferably the method is used for the prevention in a risk patient selected from a patient suffering from obesity, a patient with a positive infarct anamnesis, a patient with a positive stroke anamnesis and a patient with a family history of arterial hypertension Preferably, the hyaluronidase, the composition of the invention, the pharmaceutical composition of the invention, or the combined preparation of the invention is to be administered by the routes, dosage and treatment regimen defined above.

The skilled physician readily knows how to determine the therapeutically effective amount of hyaluronidase and of the at least one further hypertensive which will depend on the severity of the symptoms and the type of the arterial hypertension to be prevented or treated. The therapeutically effective amount will also depend on the route of administration, the idiosyncratic pharmacology, the individual patient's disease history, the other medicaments administered to the patients such as the at least one further antihypertensive mentioned above. It is likewise routine to the skilled worker to determine the therapeutically effective amount of the at least one further antihypertensive mentioned above. The success of the therapy can be easily determined by measuring the blood pressure and preferably by also monitoring the development (recession) of the other prominent symptoms of the arterial hypertension to be treated.

The following Examples are meant to illustrate the invention without being limiting.

EXAMPLES

Several patients with arterial hypertension were successfully treated with hyaluronidase. Shown below are data obtained from five patients.

Example 1: Patient 1 (A.C.)

Patient 1 suffered from coronary heart disease and displayed symptoms of angina pectoris. At that time the patient also suffered from arterial hypertension and displayed systolic blood pressure values of 180-160 mmHg and diastolic blood pressure values ranging from 120-105 mmHg.

Before hyaluronidase treatment was initiated, patient 1 had been treated for arterial hypertension with the following medicaments:
- 1 tablet per day Belok Zok 100 mg (Metoprolol 100 mg), a ß1-adrenergic receptor antagonist;
- 1 tablet per day Atacand 16 mg Plus (Candesartan 16 mg+12.5 mg hydrochlorthiazide), an angiotensin II receptor inhibitor;
- 1 tablet per day Unimax 5/5 (Felodipin 5 mg, a $Ca^{++}$ channel antagonist); and
- 1 tablet per day 5 mg Ramipril (an ACE antagonist).

Based on this regimen the blood pressure could be kept at a normal level. Hyaluronidase treatment was initiated 3 Nov. 1995 by combining the above treatment regimen (Belok Zok 100 mg+Atacand 16 mg Plus+Unimax 5/5) with the following dosis regimen of Hyaluronidase:

TABLE 1

| Hylase dosage regimen | |
|---|---|
| Date | Hylase dosage (Hylase Dessau 1.500 IU product, by RIEMSER Arzneimittel AG), intravenous injection |
| 3 Nov. 1995 | 4.500 IU |
| 4 Nov. 1995 | 6.000 IU |
| 5 Nov. 1995 | 7.500 IU |

Then, the above co-treatment regimen with (daily administration of each of Belok Zok+Atacand 16 mg Plus+Unimax 5/5 at the dosages indicated above) and hyaluronidase (7.500 IU per day) administered 5× per week for six weeks was continued until the end of December 1995.

From January 1996 on the above treatment regimen could be surprisingly reduced as follows, while at the same time maintaining the blood pressure levels at a normal level (see table 2 below):
- 0.25 tablet per day Belok Zok 100 mg (Metoprolol 100 mg), a ß1-adrenergic receptor antagonist;
- 0.5 tablet per day Atacand 16 mg Plus (Candesartan 16 mg+12.5 mg hydrochlorthiazide), an angiotensin II receptor inhibitor; and
- 5 times a week Hylase Dessau 7.500 IU by intravenous injection.

This regimen was applied from January to May 1996.

From June 1996 on Hylase therapy was discontinued and the patient maintained normal blood pressure levels with the following medication:
- 0.25 tablet per day Atacand 16 mg (Candesartan 16 mg), an angiotensin II receptor inhibitor.

Thus, hyaluronidase exerted a strong blood pressure-reducing effect which allowed to reduce administration of the other antihypertensives used before hyaluronidase treatment was initiated. From the day hyaluronidase treatment was initiated, patient 1 displayed stable and normal blood pressure values. As a result of the hyaluronidase co-administration the systolic blood pressure value ranged between 130 and 120 mmHg and the diastolic values between 80-65 mmHg.

TABLE 2

| Riva-Rocci values (determined on the upper arm using the Scipione Riva-Rocci method) (RR Values): | |
|---|---|
| Date | Blood Pressure systolic pressure/diastolic pressure [mmHg] |
| 2 Nov. 1995 | 150/110 |
| End of November 1995 | 140/88 |
| End of December 1995 | 142/79 |
| 2 Jan. 2008 | 137/66 |
| 11 Jun. 2008 | 168/75 |
| 17 Jul. 2008 | 172/79 |

Example 2: Patient 2 (H.L.)

Immediately before hyaluronidase therapy was initiated, Patient 2 was diagnosed as suffering from arterial hypertension with symptoms of angina pectoris. Patient 2 also suffered from coronary heart disease and a heart catheter-based examination carried out Mar. 10, 2008 confirmed that the heart vessels still showed stenosis and calcification. At that time patient 2 displayed systolic blood pressure values of 190-170 mmHg and diastolic blood pressure values ranging from 125-100 mmHg.

Before hyaluronidase treatment commenced, patient 2 had been treated for arterial hypertension with the following medicaments:
- 1 tablet per day Atacand 16 mg Plus (Candesartan 16 mg+12.5 mg hydrochlorthiazide), an angiotensin II receptor inhibitor;
- 1 tablet per day Amlopidin 10 mg, a $Ca^{++}$ channel antagonist; and
- 1 tablet per day Nebilit (Nebivolol 5 mg), a ß1-Adrenergic receptor antagonist.

Hyaluronidase was co-administered by intravenous injection on top of the above regimen from 28 Apr. 2008 to 28 May 2008.

TABLE 3

| Hylase dosage regimen | |
|---|---|
| Date | Hylase dosage (Hylase Dessau 1.500 IU product, by RIEMSER Arzneimittel AG), intravenous injection |
| 28 Apr. 2008 | 4.500 IU |
| 29 Apr. 2008 | 6.000 IU |
| 30 Apr. 2008 | 7.500 IU |
| 2 May 2008 | 9.000 IU |
| 3 May 2008 | 9.000 IU |
| 4 May 2008 | 9.000 IU |
| 5 May 2008 | 9.000 IU |
| 6 May 2008 | 9.000 IU |
| 7 May 2008 | 9.000 IU |
| 8 May 2008 | 10.500 IU |
| 9 May 2008 | 10.500 IU |
| 13 May 2008 | 10.500 IU |
| 27 May 2008 | 10.500 IU |
| 28 May 2008 | 10.500 IU |

As a result of the hyaluronidase therapy the symptoms of angina pectoris disappeared and the blood pressure fell significantly and persistently to a systolic blood pressure value ranging between 140-120 mmHg and diastolic values between 80-60 mmHg.

Moreover, following termination of the Hyaluronidase therapy the above medication regimen used before the hylase co-administration therapy could be reduced to the following treatment:

1 tablet per day Nebilit (Nebivolol 5 mg), 0.5 tablets, a ß1-Adrenergic receptor antagonist;

Using only Nebilit medication, the patient steadily displayed normal diastolic blood pressure values of less than 80 mmHg. The patient still displayed the normal blood pressure values in the months following the termination of the antihypertensives/hyaluronidase administration.

TABLE 4

| RR Values: | |
| --- | --- |
| Date | Blood Pressure systolic pressure/diastolic pressure [mmHg] |
| 6 May 2008 | 108/73 |
| 7 May 2008 | 120/74 |
| 13 May 2008 | 115/75 |
| 20 May 2008 | 136/79 |

Thus, Hyaluronidase exerted long-lasting and strong blood pressure-reducing effect which allowed to dramatically reduce the administration of the other antihypertensives used before hyaluronidase treatment was initiated.

Example 3: Patient 3 (Z.M.)

The patient was diagnosed as suffering from, coronary heart disease, obstructive disease, condition after myocard infarct, general arteriosclerosis.

Before hyaluronidase treatment was initiated, patient 3 had been treated for hypertension with the following medicaments:

1 tablet per day Belok Zok mite (11.88 mg);
1 tablet per day Enalapril (10 mg);
1 tablet every 3 days Plavix (75 mg Clopidogrel); and
1 tablet per day Norvasc (5 mg).

At that time the patient displayed systolic blood pressure values of 156-147 mmHg and diastolic blood pressure values ranging from 80-66 mmHg.

Hyaluronidase co-administration on top of the above treatment and was carried out from 19 Jun. 2008 to 30 Jun. 2008 by intravenous injection using the following dosage regimen for hylase:

TABLE 5

| Hylase dosage regimen | |
| --- | --- |
| Date | Hylase dosage (Hylase Dessau 1.500 IU product, by RIEMSER Arzneimittel AG), intravenous injection |
| 19 Jun. 2008 | 4.500 IU |
| 20 Jun. 2008 | 6.000 IU |
| 21 Jun. 2008 | 7.500 IU |
| 22 Jun. 2008 | 9.000 IU |
| 23 Jun. 2008 | 10.500 IU |
| 24 Jun. 2008 | 12.000 IU |
| 25 Jun. 2008 | 12.000 IU |
| 26 Jun. 2008 | 12.000 IU |
| 27 Jun. 2008 | 15.000 IU |
| 28 Jun. 2008 | 15.000 IU |
| 29 Jun. 2008 | 15.000 IU |
| 30 Jun. 2008 | 15.000 IU |

Medication after Hyaluronidase Therapy was Discontinued:

1× every 3 days Plavix 75 mg (Clopidogrel), a thrombozyte aggregation inhibitor.

Thus, due to the Hyaluronidase therapy the administration of blood pressure reducing-medicaments could be discontinued while maintaining normal blood pressure levels.

TABLE 6

| RR- Values | |
| --- | --- |
| Date | Blood Pressure systolic pressure/diastolic pressure [mmHg] |
| 8 May 2008 | 156/80 |
| 9 May 2008 | 147/66 |
| 19 Jun. 2008 | 153/64 |
| 20 Jun. 2008 | 134/61 |
| 24 Jun. 2008 | 163/67 |
| 25 Jun. 2008 | 157/70 |
| 27 Jun. 2008 | 135/66 |
| 25 Jul. 2008 | 130/70 |

Example 4: Patient 4 (N.H.)

The patient was diagnosed as suffering from arteriosclerosis, arterial hypertension, and obesity. At that time the patient displayed systolic blood pressure values of 160-140 mmHg and diastolic blood pressure values ranging from 110-100 mmHg.

Medication Before Hyaluronidase Therapy was Initiated

1× per day Atacand 16 mg, an angiotensin II receptor inhibitor; and

1× per day Atenolol 25 mg (beta adrenergic receptor inhibitor)

Hyaluronidase co-administration was carried out from 10 Jul. 2007 to 9 Nov. 2007. On top of the above treatment regimen, hylase was administered according to the following dosage regimen:

TABLE 7

| Hylase dosage regimen | |
| --- | --- |
| Date | Hylase dosage (Hylase Dessau 1.500 IU product, by RIEMSER Arzneimittel AG), intravenous injection |
| 10 Oct. 2007 | 6.000 |
| 11 Oct. 2007 | 7.500 |
| 14 Oct. 2007 | 9.000 |
| 15 Oct. 2007 | 10.500 |
| 5 Nov. 2007 | 10.500 |
| 6 Nov. 2007 | 10.500 |
| 7 Nov. 2007 | 12.000 |
| 8 Nov. 2007 | 12.000 |
| 9 Nov. 2007 | 12.000 |

Medication after Hyaluronidase Therapy was Terminated

1× per day Atenolol 25 mg

As a result of the Hyaluronidase administration the systolic blood pressure value ranged between 130 and 120 mmHg and the diastolic values between 80-70 mmHg and the administration of antihypertensives could be was dramatically reduced.

TABLE 8

RR Values:

| Date | Blood Pressure systolic pressure/diastolic pressure [mmHg] |
|---|---|
| 7 Aug. 2007 | 132/69 |
| 8 Aug. 2007 | 111/58 |
| 9 Oct. 2007 | 126/81 |
| 10 Oct. 2007 | 123/87 |
| 11 Oct. 2007 | 120/80 |
| 6 Nov. 2007 | 122/74 |
| 7 Nov. 2007 | 147/77 |
| 8 Nov. 2007 | 123/78 |
| 9 Nov. 2007 | 122/80 |
| 1 Aug. 2008 | 110/68 |

Example 5: Patient 5 (T.F.)

The patient was diagnosed as suffering from coronary heart disease, arterial hypertension, condition after pericarditis, aortic valve stenosis, hypertrophic cardiomyopathy, arterial fibrillation and condition after apoplexy.

Medication Before Hyaluronidase Therapy was Initiated
  1 tablet per day of Atacand 16/12.5 mg;
  1 tablet per day Diblocin Pb 4 mg; and
  1 tablet per day Belok Zok Mite 47.5 mg.

At that time the patient displayed systolic blood pressure values of 174-152 mmHg and diastolic blood pressure values ranging from 107-98 mmHg.

Hyaluronidase co-administration on top of the above regimen was initiated 9 Dec. 2002 and was continued until 17 Dec. 2002.

TABLE 9

Hylase dosage regimen

| Date | Hylase dosage (Hylase Dessau 1.500 IU product, by RIEMSER Arzneimittel AG), intravenous injection |
|---|---|
| 9 Dec. 2002 | 4.500 IU |
| 10 Dec. 2002 | 6.000 IU |
| 11 Dec. 2002 | 7.500 IU |
| 12 Dec. 2002 | 9.000 IU |
| 13 Dec. 2002 | 10.500 IU |
| 14 Dec. 2002 | 12.000 IU |
| 16 Dec. 2002 | 12.000 IU |
| 17 Dec. 2002 | 13.500 IU |

Medication after Hyaluronidase Therapy was Discontinued (from 18 Dec. 2002 on):
  0.5 tablet per day Belok Zok Mite 47.5 mg.

As a result of the hyaluronidase administration the systolic blood pressure value ranged between 188-128 mmHg and the diastolic values between 94-69 mmHg.

TABLE 10

RR Values:

| Date | Blood Pressure systolic pressure/diastolic pressure [mmHg] |
|---|---|
| 15 Jan. 2002 | 174/103 |
| 2 Dec. 2002 | 153/96 |
| 3 Dec. 2002 | 152/107 |
| 9 Dec. 2002 | 170/98 |
| 12 Dec. 2002 | 145/88 |
| 30 Jan. 2003 | 128/83 |

TABLE 10-continued

RR Values:

| Date | Blood Pressure systolic pressure/diastolic pressure [mmHg] |
|---|---|
| 13 Feb. 2003 | 143/85 |
| 14 Apr. 2003 | 113/69 |
| 2 Aug. 2004 | 148/80 |

The invention claimed is:

1. A method of treating arterial hypertension in a mammalian individual having chronically elevated blood pressure, the method comprising administering to the individual hyaluronidase in an amount of at least 3,000 IU of hyaluronidase per day.

2. The method of claim 1, wherein the arterial hypertension is endocrine hypertension, essential hypertension, arteriosclerotic hypertension, cardiovascular hypertension, renal hypertension, labile hypertension, neurogenic hypertension, paroxysmal hypertension, portal hypertension, pulmonary hypertension, or secondary hypertension.

3. The method of claim 1, wherein the individual is a non-human mammal or a human.

4. The method of claim 1, wherein the hyaluronidase is administered parenterally.

5. The method of claim 1, wherein the hyaluronidase is administered by an enteral route.

6. The method of claim 1, wherein the hyaluronidase is administered at a frequency of from 1 time per week to 7 times per week.

7. The method of claim 1, wherein the hyaluronidase is administered for a period of time of at least 2 weeks.

8. The method of claim 1, wherein the hyaluronidase dosage is increased over time until a plateau dosage of about 10,000 IU to about 15,000 IU is reached.

9. The method of claim 1, further comprising administering at least one additional antihypertensive agent.

10. The method of claim 9, wherein the at least one further antihypertensive agent is selected from a diuretic, an alpha-adrenergic receptor inhibitor, a beta adrenergic receptor inhibitor, an angiotensin converting enzyme inhibitor, an angiotensin receptor inhibitor, a renin inhibitor, a calcium-channel inhibitor, a vasodilating agent, an antisympathotonic and an imidazoline type 1 receptor agonist.

11. The method of claim 9, wherein the hyaluronidase and the at least one additional antihypertensive are administered simultaneously.

12. The method of claim 9, wherein the hyaluronidase and the at least one additional antihypertensive are administered at separate times.

13. The method of claim 1, wherein said administering is effective to reduce diastolic blood pressure in the individual by at least 5 mm Hg and/or to reduce systolic blood pressure in the individual by at least 5 mm Hg.

14. The method of claim 1, wherein said administering is effective to reduce diastolic blood pressure in the individual by at least 10 mm Hg and/or to reduce systolic blood pressure in the individual by at least 10 mm Hg.

15. The method of claim 1, wherein at least 3000 IU of hyaluronidase are administered per day, at a frequency of 1 to 7 days per week, for a period of at least 1 week.

16. The method of claim 13, wherein the hyaluronidase dosage is increased over the course of administration to a daily dosage of about 10,000 IU to about 15,000 IU.

17. The method of claim 1, wherein at least 4500 IU of hyaluronidase are administered per day, at a frequency of 3 to 7 days per week, for a period of at least 2 weeks.

18. The method of claim 15, wherein the hyaluronidase dosage is increased over the course of administration to a daily dosage of about 10,000 IU to about 15,000 IU.

19. The method of claim 1, wherein at least 6000 IU of hyaluronidase are administered per day, at a frequency of 3 to 7 days per week, for a period of at least 2 weeks.

20. The method of claim 17, wherein the hyaluronidase dosage is increased over the course of administration to a daily dosage of about 10,000 IU to about 15,000 IU.

* * * * *